United States Patent
Hunter et al.

(10) Patent No.: US 6,499,488 B1
(45) Date of Patent: Dec. 31, 2002

(54) SURGICAL SENSOR

(75) Inventors: Mark W. Hunter, Broomfield, CO (US); Sheri McCoid, Broomfield, CO (US); Paul Kessman, Broomfield, CO (US)

(73) Assignees: Winchester Development Associates, Winchester, MA (US); Enterprise Medical Technology, Cambridge, MA (US)

( * ) Notice: Subject to any disclaimer, the term of this patent is extended or adjusted under 35 U.S.C. 154(b) by 0 days.

(21) Appl. No.: 09/428,721

(22) Filed: Oct. 28, 1999

(51) Int. Cl.[7] .............................................. A61B 19/00
(52) U.S. Cl. ..................................................... 128/899
(58) Field of Search ................................ 128/899, 898; 600/300, 424; 606/158, 72; 433/174, 182, 229

(56) References Cited

U.S. PATENT DOCUMENTS

| | | |
|---|---|---|
| 2,650,588 A | 9/1953 | Drew |
| 4,328,813 A | 5/1982 | Ray |
| 4,618,978 A | 10/1986 | Cosman |
| 4,621,628 A | 11/1986 | Brudermann |
| 4,645,343 A | 2/1987 | Stockdale et al. |
| 4,673,352 A | 6/1987 | Hansen |
| 4,706,665 A | 11/1987 | Gouda |
| 4,722,056 A | 1/1988 | Roberts et al. |
| 4,793,355 A | 12/1988 | Crum et al. |
| 4,803,976 A | 2/1989 | Frigg et al. |
| 4,821,731 A | 4/1989 | Martinelli et al. |
| 4,836,778 A | 6/1989 | Baumrind et al. |
| 4,923,459 A | 5/1990 | Nambu |
| 4,931,056 A | 6/1990 | Ghajar et al. |
| 4,945,914 A | 8/1990 | Allen |

(List continued on next page.)

FOREIGN PATENT DOCUMENTS

| | | |
|---|---|---|
| DE | 3831278 A1 | 3/1989 |
| DE | 42 33 978 C1 | 4/1994 |
| EP | 0 319 844 A1 | 1/1988 |
| EP | 0 651 968 A1 | 8/1990 |
| EP | 0 655 138 B1 | 8/1993 |
| EP | 0 894 473 A2 | 1/1995 |
| WO | WO 94/04938 | 3/1994 |
| WO | WO 98/08554 | 3/1998 |
| WO | WO 99/60939 | 12/1999 |

OTHER PUBLICATIONS

Laitinen, Lauri V., "Noninvasive multipurpose stereo-adapter," Neurological Research, Jun. 1987, pp. 137–141.

Kelly, Patrick J., Kall, Bruce A. et al., "Computer–assisted stereotaxic laser resection of intra–axial brain neoplasms, J. Neurosurg.," vol. 64, Mar. 1986, pp. 427–439.

Laitinen, Lauri V., Liliequist, Bengt, et al., "An Adapter for Computed Tomography–Guided, Stereotaxis," Surg. Neurol., 1985, pp. 559–566.

Horner, Neil and Potts, Gordon D., "A Comparison of CT–Stereotaxic Brain Biopsy Techniques," Investigative Radiology, Sep.–Oct. 1984, pp. 367–373.

(List continued on next page.)

*Primary Examiner*—Kevin Shaver
*Assistant Examiner*—Brian Szmal
(74) *Attorney, Agent, or Firm*—McDermott, Will & Emery

(57) ABSTRACT

An integrated surgical anchor/localization sensor is disclosed. The anchor is adapted to be secured to an anatomical structure and contains a sensor housing. A receiver is located within the sensor housing and is adapted to sense reference signals generated by a surgical guidance system. A transmitter, connected to the receiver, conveys to a processor signals received by the receiver, so that the signals transmitted by the receiver are indicative of a current position of the anchor. Various other structures and methods are also disclosed.

26 Claims, 4 Drawing Sheets

U.S. PATENT DOCUMENTS

| | | |
|---|---|---|
| 4,951,653 A | 8/1990 | Fry et al. |
| 4,991,579 A | 2/1991 | Allen |
| 5,059,789 A | 10/1991 | Salcudean |
| 5,094,241 A | 3/1992 | Allen |
| 5,097,839 A | 3/1992 | Allen |
| 5,099,845 A | 3/1992 | Besz et al. |
| 5,119,817 A | 6/1992 | Allen |
| 5,160,337 A | 11/1992 | Cosman |
| 5,178,164 A | 1/1993 | Allen |
| 5,186,174 A | 2/1993 | Schlöndorff et al. |
| 5,197,965 A | 3/1993 | Cherry et al. |
| 5,198,877 A | 3/1993 | Schulz |
| 5,211,164 A | 5/1993 | Allen |
| 5,211,176 A | 5/1993 | Ishiguro et al. |
| 5,222,499 A | 6/1993 | Allen et al. |
| 5,249,581 A | 10/1993 | Horbal et al. |
| 5,251,127 A | 10/1993 | Raab |
| 5,265,611 A | 11/1993 | Hoenig et al. |
| 5,279,309 A | 1/1994 | Taylor et al. |
| 5,295,483 A | 3/1994 | Nowacki et al. |
| 5,299,254 A | 3/1994 | Dancer et al. |
| 5,305,091 A | 4/1994 | Gelbart et al. |
| 5,305,203 A | 4/1994 | Raab |
| 5,309,913 A | 5/1994 | Kormos et al. |
| 5,315,630 A | 5/1994 | Sturm et al. |
| 5,368,030 A | 11/1994 | Zinreich et al. |
| 5,383,454 A | 1/1995 | Bucholz |
| 5,389,101 A | 2/1995 | Heilbrun et al. |
| 5,391,199 A | 2/1995 | Ben-Haim |
| 5,394,457 A | 2/1995 | Leibinger et al. |
| 5,397,329 A | 3/1995 | Allen |
| 5,402,801 A | 4/1995 | Taylor |
| 5,429,132 A | 7/1995 | Guy et al. |
| 5,443,489 A | 8/1995 | Ben-Haim |
| 5,464,446 A | 11/1995 | Dreessen et al. |
| 5,480,422 A | 1/1996 | Ben-Haim |
| 5,483,961 A | 1/1996 | Kelly et al. |
| 5,490,196 A | 2/1996 | Rudich et al. |
| 5,494,034 A | 2/1996 | Schlöndorff et al. |
| 5,515,160 A | 5/1996 | Schulz et al. |
| 5,517,990 A | 5/1996 | Kalfas et al. |
| 5,546,951 A | 8/1996 | Ben-Haim |
| 5,551,429 A | 9/1996 | Fitzpatrick et al. |
| 5,558,091 A | 9/1996 | Acker et al. |
| 5,568,809 A | 10/1996 | Ben-Haim |
| 5,575,794 A | 11/1996 | Walus et al. |
| 5,588,430 A | 12/1996 | Bova et al. |
| 5,592,939 A | 1/1997 | Martinelli |
| 5,595,193 A | 1/1997 | Walus et al. |
| 5,603,318 A | 2/1997 | Heilbrun et al. |
| 5,617,857 A | 4/1997 | Chader et al. |
| 5,622,170 A | 4/1997 | Schulz |
| 5,662,111 A | 9/1997 | Cosman |
| 5,676,673 A | 10/1997 | Ferre et al. |
| 5,695,500 A | 12/1997 | Taylor et al. |
| 5,695,501 A | 12/1997 | Carol et al. |
| 5,697,377 A | 12/1997 | Wittkampf |
| 5,711,299 A | 1/1998 | Manwaring et al. |
| 5,727,553 A | 3/1998 | Saad |
| 5,729,129 A | 3/1998 | Acker |
| 5,730,130 A | 3/1998 | Fitzpatrick et al. |
| 5,742,394 A | 4/1998 | Hansen |
| 5,748,767 A | 5/1998 | Raab |
| 5,752,513 A | 5/1998 | Acker et al. |
| RE35,816 E | 6/1998 | Schulz |
| 5,762,064 A | 6/1998 | Polvani |
| 5,769,861 A | 6/1998 | Vilsmeier |
| 5,772,594 A | 6/1998 | Barrick |
| 5,787,886 A | 8/1998 | Kelly et al. |
| 5,797,849 A | 8/1998 | Vesely et al. |
| 5,799,099 A | 8/1998 | Wang et al. |
| 5,800,352 A | 9/1998 | Ferre et al. |
| 5,823,958 A | 10/1998 | Truppe |
| 5,829,444 A | 11/1998 | Ferre et al. |
| 5,833,608 A | 11/1998 | Acker |
| 5,836,954 A | 11/1998 | Heilburn et al. |
| 5,840,025 A | 11/1998 | Ben-Haim |
| 5,848,967 A | 12/1998 | Cosman |
| 5,851,183 A | 12/1998 | Bucholz |
| 5,871,445 A | 2/1999 | Bucholz |
| 5,871,455 A | 2/1999 | Ueno |
| 5,873,822 A | 2/1999 | Ferre et al. |
| 5,884,410 A | 3/1999 | Prinz |
| 5,891,034 A | 4/1999 | Bucholz |
| 5,904,691 A | 5/1999 | Barnett et al. |
| 5,907,395 A | 5/1999 | Schultz et al. |
| 5,913,820 A | 6/1999 | Bladen et al. |
| 5,920,395 A | 7/1999 | Schultz |
| 5,921,992 A | 7/1999 | Costales et al. |
| 5,947,981 A | 9/1999 | Cosman |
| 5,954,647 A | 9/1999 | Bova et al. |
| 5,971,997 A | 10/1999 | Guthrie et al. |
| 5,980,535 A | 11/1999 | Barnett et al. |
| 5,987,960 A | 11/1999 | Messner et al. |
| 5,999,837 A | 12/1999 | Messner et al. |
| 5,999,840 A | 12/1999 | Grimson et al. |
| 6,006,126 A | 12/1999 | Cosman |
| 6,332,089 B1 * | 12/2001 | Acker et al. ................ 600/424 |

OTHER PUBLICATIONS

Heilbrun, Peter M., Roberts, Theodore S., et al., "Preliminary experience with Brown–Roberts–Wells (BRW) computerized tomography stereotaxic guidance system," J. Neurosurg. vol. 59, Aug. 1983, pp. 217–222.

Leksell, L. and Jernberg, B., "Stereotaxis and Tomography A Technical Note," 1980, Acta Neurochururgica 52, pp. 1–7.

The Laitinen Stereotactic System, E–2—E6.

Bucholz, Richard D., Ho, Hector W., and Rubin, Jason P., "Variables affecting the accuracy of stereotactic localization using computerized tomography," J. Neurosurg., vol. 79, Nov. 1993, pp. 667–673.

Foley, Kevin T., "The StealthStation™: Three Dimensional Image–Interactive Guidance for the Spine Surgeon," Spinal Frontiers, Apr. 1996, pp. 7–9.

Barrick, E. Frederick and Mulhern, Peter J., "Technical Difficulties with the Brooker—Wills Nail in Acute Fractures of the Femur," J. of Orthopaedic Trauma, vol. 4, 1990, pp. 144–150.

Barrick, E. Frederick, "Distal Locking Screw Insertion Using a Cannulated Drill Bit: Technical Note," Journal of Orthopaedic Trauma, vol. 7, 1993, pp. 248–251.

Smith, Kurt R., Frank, Kevin J., and Bucholz, Richard D., "The *Neurostation*™—A Highly Accurate, Minimally Invasive Solution to Frameless Stereotactic Neurosurgery," Computerized Medical Imaging and Graphics, vol. 18, Jul.–Aug. 1994, pp. 247–256.

* cited by examiner

SURGICAL SENSOR

CONCURRENTLY FILED APPLICATIONS

The following United States patent applications, which were concurrently filed with this one on Oct. 28, 1999, are fully incorporated herein by reference: Method and System for Navigating a Catheter Probe in the Presence of Field-influencing Objects, by Michael Martinelli, Paul Kessman and Brad Jascob; Patient-shielding and Coil System, by Michael Martinelli, Paul Kessman and Brad Jascob; Navigation Information Overlay onto Ultrasound Imagery, by Paul Kessman, Troy Holsing and Jason Trobaugh; Coil Structures and Methods for Generating Magnetic Fields, by Brad Jascob, Paul Kessman and Michael Martinelli; Registration of Human Anatomy Integrated for Electromagnetic Localization, by Mark W. Hunter and Paul Kessman; System for Translation of Electromagnetic and Optical Localization Systems, by Mark W. Hunter and Paul Kessman; and Surgical Communication and Power System, by Mark W. Hunter, Paul Kessman and Brad Jascob.

BACKGROUND OF THE INVENTION

1. Field of the Invention

The present invention relates to a surgical sensor which may be integrated with an anatomical anchor. The sensor has particular applicability in surgical procedures where it is desirable to track the relative movement of one or more structures.

2. Description of the Related Art

Many surgical procedures are planned and guided using images obtained from imaging systems such as magnetic resonance imagers (MRIs), computer tomographic imagers (CTs), x-ray imagers, position emission tomographic (PET) scanners, and photo-emission computer technology (SPECT). These systems permit physicians to obtain detailed preoperative (or intraoperative) views of anatomical structures using noninvasive procedures. Once these images are obtained, the physician typically uses the images to plan a corrective surgical procedure. With the patient lying on an operating table, the images may be "registered" with the corresponding physical space of the patient, and displayed on a screen in the operating room (OR). As the physician navigates probes or other medical instruments within the patient, sensors on the instruments relay positional information to a computer. The computer, in turn, overlays a display of the position of the instrument on the image of the anatomical structure. In this way, the physician may navigate through a surgical procedure by viewing a display screen in the OR. An example of a related art system is found in U.S. patent application Ser. No. 08/809,404, entitled: "Surgical Navigation System Including Reference and Localization Frame," and which is fully incorporated herein by reference.

Until now, the tracking of anatomical structures has been largely limited to external tracking, either by taping a sensor to a patient's skin, or by affixing an external clamp to the patient, such as a Mayfield clamp, attached externally to a patient's head.

U.S. patent application Ser. No. 08/931,654 entitled Bone Navigation System which is incorporated fully herein by reference discloses a system which employs screws extending from a bone fragment through a patient's skin and connected to a platform external to the patient. Tracking elements such as, for example, emitters are located on the platform so that when a bone fragment moves, so too does the platform with the connected tracking elements. An array in the OR tracks movement of the tracking elements, and this movement is correlated to the movement of the bone fragment, in order to precisely track the movement of the bone fragment. Alternatively, clamps may be used, in place of screws, to secure an array of tracking elements to a bone structure. While such related art systems may generally be reliable, their structure is somewhat cumbersome, especially when the movement of multiple anatomical structures needs to be tracked. In addition, the use of the tracking elements and receiving array requires an unobstructed line of sight therebetween which not only limits implantation within a patient, but also can lead to interference.

For these reasons, in procedures such as those involving the spine or the reconstruction or repair of vertebral bodies, fractured skulls, fragmented bones, or other damaged boney structures, it has been somewhat difficult to track the relative movement of multiple anatomical structures.

SUMMARY OF THE INVENTION

It is an object of certain aspects of this invention to enable the detection of anatomical structure movement during medical procedures without the use of cumbersome external equipment fixed to the patient.

It is another object of certain aspects of the invention to provide a localization system for internal and/or external anatomical structures that do not require an unobstructed line of sight between a positional sensor and a detector.

It is a further object of certain aspects of this invention to provide a localization system for internal anatomical structures which may be employed with minimal invasive procedures.

It is another object of certain aspects of this invention to provide an integrated anchor and localization sensor that may be deployed with relative ease.

It is yet another object of certain aspects of this invention to provide an anatomical anchor which may serve as both a preprocedural and intraprocedural fiducial marker.

It is an additional object of certain aspects of this invention to provide a reliable localization marker which may be placed in a patient in advance of a procedure and which may remain in the patient for a period of time following the procedure.

It is a further object of certain aspects of the present invention to enable movement detection, with five or six degrees of freedom, of an anatomical structure or surgical instrument (whether the instrument be an anchor, a catheter, or any other medical instrument).

These and other objects of the invention may be inherent or derived from the detailed description of the preferred embodiments.

The invention, in its broadest sense, may comprise one or more of the following aspects, either alone or in combination with one or more additional elements:

- an anatomical anchor/sensor,
- a receiver on an anchor for sensing signals generated external to the anchor,
- a transmitter on an anchor for conveying signals indicative of the anchor's location,
- a signal generator on an anchor,
- a connection for securing a receiver to an anatomical anchor,
- a receiver and/or transmitter on a surgical screw, staple, pin rod, needle or soft tissue anchor, an electromagnetic sensing coil on an anchor, a magnet on an anchor, an electromagnetic sensor having multiple collinear coils wound at differing angles, whether disposed on an anchor, a catheter, or other medical instrument, hard-wiring a transmitter on an anchor to a processor, affixing a wireless transmitter to an anchor, affixing a conductive electrode to an anatomical anchor, a surgical screw having a hollow containing a sensor, affixing a sensor to anchor using potting material, a sensor housing for the head of a screw, an attachable/detachable sensor mount for an anchor, a grasping region for permitting medical personnel to screw a portion of a screw/sensor into an anatomical structure, an integrated anatomical anchor/sensor where the sensor is detachable, methods and apparatuses for deploying an integrated anchor/sensor, methods for making and using the above items, procedures where the relative movement of instruments and/or anatomical structures are tracked and displayed, and any other novel and unobvious aspects of the following disclosure and/or claims.

DETAILED DESCRIPTION OF THE PREFERRED EMBODIMENTS

Figure 1A:
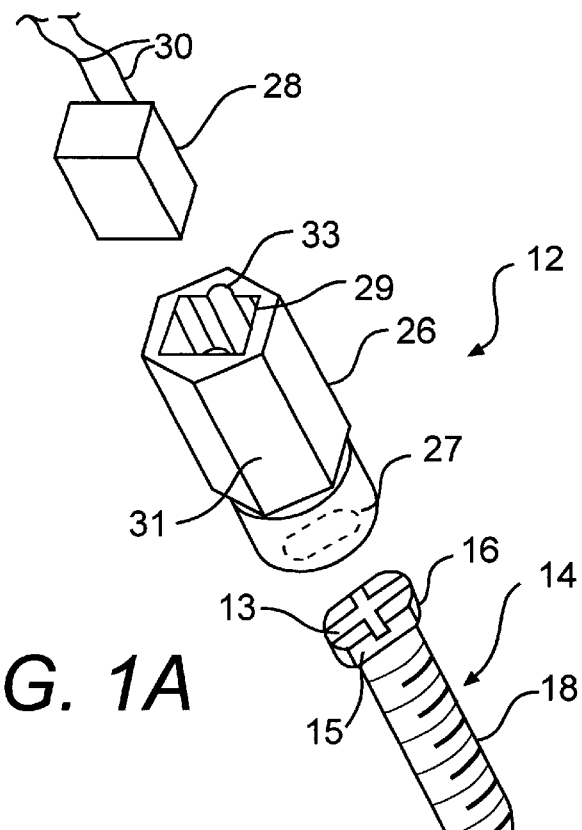
FIG. 1A is an exploded view of an integrated sensor and bone screw in accordance with one embodiment of the present invention.

The invention will now be described in connection with the Figures wherein like parts are numbered with the same reference numerals for ease of discussion.

In accordance with the invention, there is provided an integrated surgical anchor/localization sensor. An example of such an integrated unit is designated by reference number 12 in FIG. 1.

According to the invention, the anchor is configured to be secured to an anatomical structure. As illustrated in FIG. 1, an anchor in accordance with the invention may, by way of example, include a surgical screw 14. Screw 14 has a head portion 16, and a threaded portion 18. The threaded portion 18 is configured to be secured into boney structure such as portions of long bones, vertebral bodies, the skull, or any other boney anatomical structure. In an preferred embodiment, the anchor may be a 2.2 mm cross-drive screw, 3–7 mm in length. Preferably, the screw has keyed head portions 15 so that a connector may be securely fastened to it. Screw 15 may also contain slots 13 enabling the screw to be driven by various convention surgical screw drivers. It is also preferable for the screw 14 to be constructed of a material that will appear on an image scan and that will not cause interference with the surgical guidance system in which it is intended to be used. If an anchor is scanably detectable, it may alternatively be used as a fiducial marker. By way of example, when used with electromagnetic guidance systems, the screw may be constructed of aluminum.

While aspects of the invention are described herein in connection with surgical screws, the invention in its broadest sense is not so limited. Other anchors may be used in connection with the invention. By way of example only, such other anchors may include surgical staples, pins, rods, soft tissue anchors such as pigtails, and headframe (e.g., Mayfield) pins.

Figure 2A:
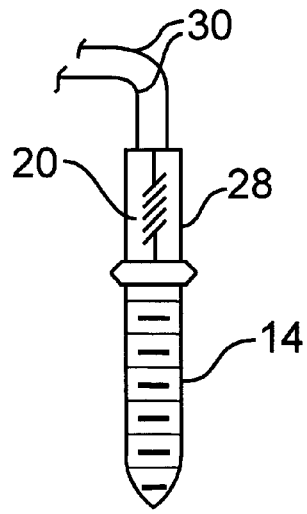
FIG. 2A is a schematic diagram of a single coil sensor in accordance with the invention.
Figure 2B:
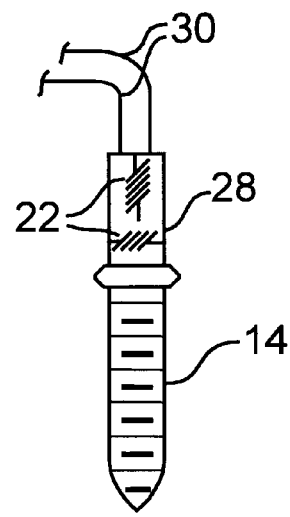
FIG. 2B is a schematic diagram of a dual-orthogonal coil sensor in accordance with the invention.
Figure 2C:
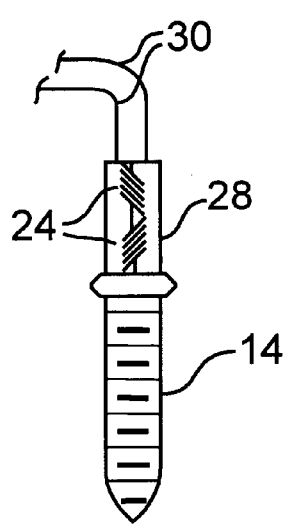
FIG. 2C is a schematic diagram of a dual-coaxial coil sensor in accordance with the invention.
Figure 3:
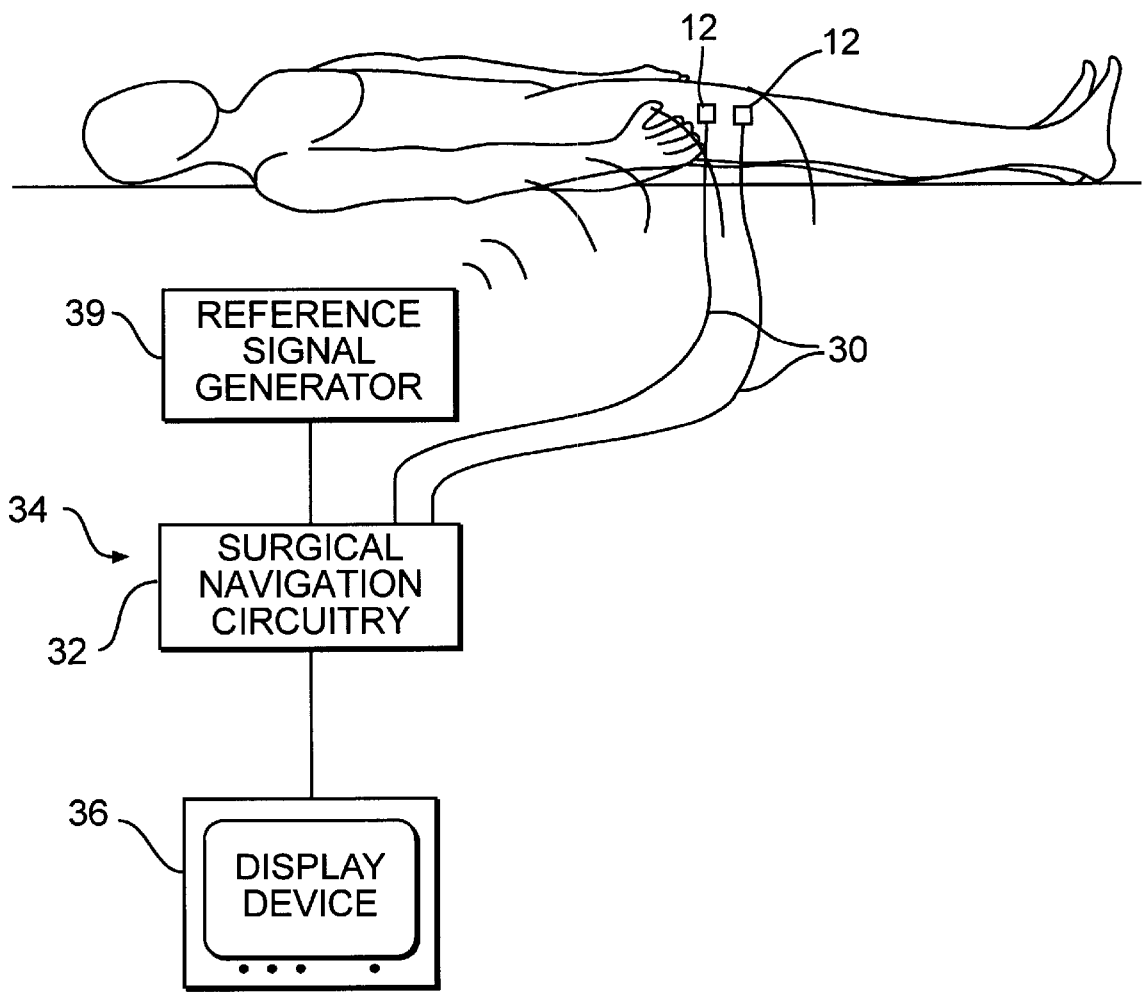
FIG. 3 is a schematic diagram of a preferred system of the invention and the environment of its use.

In accordance with the invention, there is also provided a receiver for sensing reference signals generated by a surgical guidance system. Such a system typically includes a reference signal generator 39 as schematically depicted in FIG. 3. When an electromagnetic guidance system is to be used in connection with the invention, the receiver may include at least one electromagnetic sensor 28 as schematically depicted in FIGS. 2A–2C. The invention is not limited to any specific localization guidance system or algorithm. Nevertheless, an example of an acceptable system and algorithm may be found in U.S. Pat. No. 5,592,939, entitled: "Method and System for Navigating a Catheter Probe," and which is fully incorporated herein by reference.

FIG. 2A illustrates a sensor 28 having a single coil 20. Depending on the specifics of the guidance system employed, such a sensor is typically capable of detecting position with either three or five degrees of freedom. In contrast, FIGS. 2B and 2C illustrate sensors 28 having multiple coils capable of detecting position with up to six degrees of freedom. More particularly, the coil arrangement illustrated in FIG. 2B enables a reference signal to be detected with two orthogonal sensing coils 22. Alternatively, a plurality of collinear coils may be employed. For example, in the coaxial arrangement illustrated in FIG. 2C, two collinear sensing coils 24 are wound at differing or opposing angles. While any opposing angles will work, a preferred angle is 90°. In this manner, each coil will provide unique feedback in response to the same reference signal generated by an electromagnetic guidance system.

The coil arrangement of FIG. 2C also has applicability in connection with medical devices other than anchors. For example, the collinear nature of the arrangement makes it particularly suitable for devices that have working channels such as catheters where coils of differing angles may be wrapped around the working channel to thereby minimize the size of the device.

The coil(s) of sensor 28 may be constructed of 40 AWG wire wrapped approximately 200 turns. Alternatively, the sensors may be 10 $\mu$H–1000 $\mu$H surface-mounted inductors, preferably non-shielded. In an alternative embodiment, a conductive localization system may be employed. In this situation, sensor 28 may include a conductive electrode receiver. While the preferred electromagnetic system is disclosed as including coil sensor, any electromagnetic sensor may be used including, but not limited to flux gates and reed switches.

The invention may also include a transmitter for conveying to a processor signals received by the receiver. In a preferred embodiment, the transmitter may simply include two wires 30 for hardwiring the sensor 28 to the electronics 32 of a surgical guidance system 34 (schematically illustrated in FIG. 3). The transmitter wires 30 may have, at their distal ends (not shown) connectors for selectively connecting them to the surgical guidance system 34. Preferably, the transmitter wires 30 include two pair of 40 AWG twisted bifilar wire, with an outside diameter less than about 0.062 inches. It is also preferable that the transmitter wires be compatible with sterilization processes so that they may be safely used within an anatomical body.

In an alternative embodiment, the transmitter may be wireless, transmitting signals to the surgical guidance system via radio frequency, for example. In such an embodiment, a transmitting circuit and antenna may also be part of sensor 28. Since the details of wireless transmitter systems are known in the art, for brevity, they are not repeated herein. Sensor 28 may further include a battery (not shown) for powering the transmitter. Alternatively, a voltage may be provided to the transmitter by induction using an external coil included as part of sensor 28. Examples of such systems are described in concurrently filed application Ser. No. 09/428,722, entitled "Surgical Communication and Power System" which is fully incorporated herein by reference.

As previously described, a sensor located on an anchor may receive signals from a signal generator external to the patient. The invention may, however, be embodied in a system with the reverse arrangement—i.e., element 28 being a signal generator internal to the patient and the sensor being located external to the patient. In this scenario, and if the invention uses an electromagnetic guidance system, the internal signal generator may, in its simplest form, be a magnet.

Also in accordance with the invention there may be provided a connector for securing the receiver to the anchor, the connector being configured so that the signals conveyed by the transmitter are indicative of a current position of the anchor. As embodied herein, and as illustrated in FIG. 1A, the connector may include housing 26 mounted to the head 16 of screw 14. Housing 26 may include wire relief groove 33 for transmitter wires 30. Housing 26 may also include a keyed opening 27 for receiving corresponding keyed screw head 16. This keyed arrangement prevents housing 26 from rotating on screw 14, thereby ensuring that the sensor 28 remains in a fixed position to provide an accurate reading of the position (i.e., location and/or orientation) of screw 14. Housing 26 preferably has a plurality of flat grasping surfaces 31 enabling the screw to be driven into a boney structure by manipulating the housing 26. Housing 26 may be either detachable, fixedly secured to, or integrally formed with screw 14, so long as it satisfies the function of securing a sensor to the screw. To this end, housing 26 may contain an opening 29 opposite keyed opening 27, for receiving sensor 28. If housing 26 is integrally formed with screw 14, slots 13 may be eliminated or alternatively located at the surface of opening 29.

Figure 1B:
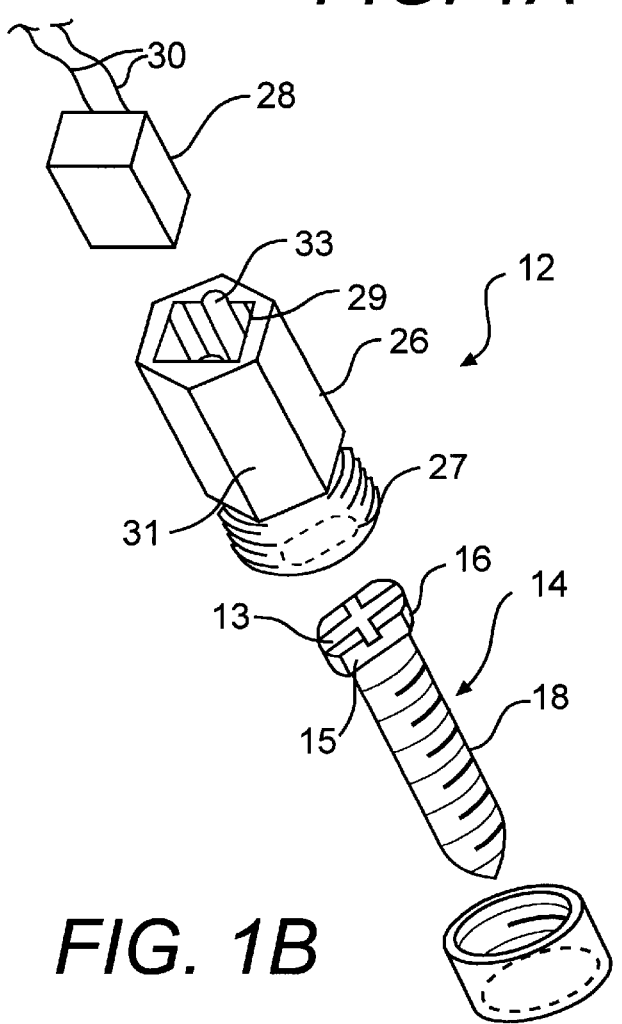
FIG. 1B is an exploded view of an integrated sensor and bone screw in accordance with another embodiment of the present invention.

FIG. 1B illustrates an arrangement similar to FIG. 1A, except that a threaded cap 17 screws onto threaded end 19 of housing 26, securing head 16 of screw 14 to housing 26. With this arrangement, sensor housing 26 may be selectively removed from screw 14.

Sensor 28 may be secured to housing 26 in any appropriate manner. For example, it may snap fit and/or be glued into opening 29. Alternatively, coils or other sensors may be deposited in opening 29 and the opening thereafter filled with a suitable potting material, such as surgical cement. In its broadest sense, the connector of the invention may be any material or mechanism capable of joining the receiver to the anchor, ranging form a quantity of potting material to structures which are molded, mechanically attached to, bonded to, or integrally formed with the anchor.

In an alternative embodiment (not shown) screw 14 may have a partially hollowed construction in lieu of the housing 26, and the receiver may be contained within the hollow. In such an embodiment, the connector may be potting material for securing the receiver within the hollow or may include a cartridge for removably securing the sensor in the hollow. In fact, removability of the sensor from the anchor may be beneficially incorporated into mechanical linkages to provide the physician with flexibility to attached and detach the sensor as the physician sees fit.

Figures 4A, 4B:
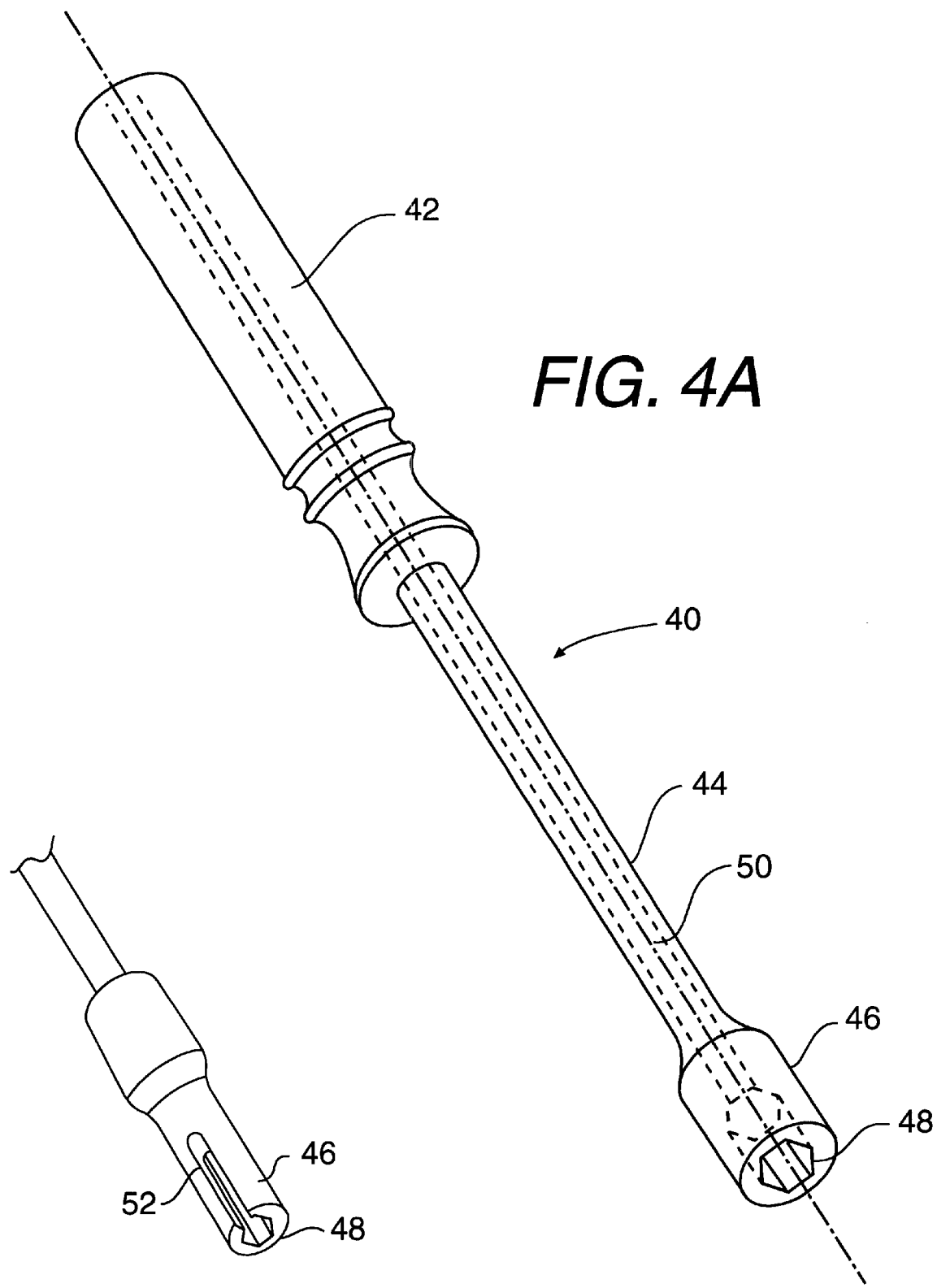
FIG. 4A is a perspective view of an embodiment of a driver associated with deploying the integrated sensors of FIGS. 1A and 1B.
FIG. 4B is a perspective of another embodiment of a driver associated with deploying the integrated sensors of FIGS. 1A and 1B.

While the anchor/sensor of the invention may be used as a fiducial marker, it has particular advantage for use in tracking boney anatomical structures such as vertebral bodies during spinal procedures or bone fragments during reconstructive procedures. By way of example, a physician may obtain an image of a fractured long bone using fluoroscopy or any other imaging device. Using a device such as cannulated driver 40 (illustrated in FIGS. 4A and 4B), the physician may implant screw/sensor into a boney structure. Specifically, driver 40 includes handle 42, neck 44, and socket 46. Socket 46 includes opening 48 shaped to engage grasping surfaces 31 of integrated screw/sensor 12. Driver 40 may include a cannula or opening 50 extending therethrough to accommodate transmitting wires 30. Alternatively, in lieu of opening 50, a slot 52 (FIG. 4B) in an edge of socket 46 may be provided to permit wires 30 to pass therethrough. In use, the physician loads a screw/sensor 12 into socket 48, and passes the loaded socket through an incision adjacent boney structure in which the screw is to be secured. Using handle 42, the physician turns the screw, securing it to the boney structure. Thereafter, the physician removes the driver 40, pulling it over the transmitting wires extended through opening 50 (FIG. 4A) or pulling the slot 52 (FIG. 46) away from wires 30.

After screwing an anchor/sensor 12 into each of the bone fragments, the sensors are then registered with the image, such as in a known manner. With the scanned image appearing on a display device 36, the physician may manipulate the fractured bone fragments, tracking their movement in real-time. This is achievable because the surgical navigation circuitry 32, receiving signals from anchor/sensors 12 in each fractured bone segment, can alter the image appearing on display 36 to reflect a current position of the bone segments. For example, the scanned image may be digitized and correlated to sensors 28 so that as the fractured portions of a bone are moved, simulated movement of those portions occur on display 36. In this way, a physician may precisely reset a fractured bone. Related procedures are disclosed in pending patent application Ser. No. 08/809,404, entitled "Surgical Navigation System Including Reference Frame and Localization Frame," and Ser. No. 08/931,654, entitled "Bone Navigation System," both of which are fully incorporated herein by reference.

It will be apparent to those skilled in the art that various modifications and variations can be made to the structure and methodology of the present invention without departing from the scope or spirit of the invention. In view of the foregoing, it is intended that the present invention cover modifications and variations of this invention provided they fall within the scope of the following claims and their equivalents.

What is claimed is:

1. An integrated surgical anchor/localization sensor, comprising:
    an anchor adapted to be secured to an anatomical structure;
    a receiver, for sensing signals generated by a surgical guidance system, wherein the receiver includes a plurality of collinear electromagnetic coils wound at differing angles;
    a transmitter coupled to the receiver, for conveying to a processor signals received by the receiver; and
    a connector for securing at least the receiver to the anchor, the connector being configured so that the signals conveyed by the transmitter are indicative of a current position of the anchor.

2. The integrated surgical anchor/localization sensor as set forth in claim 1, wherein at least the receiver is located in a cavity integral with the anchor.

3. The integrated surgical anchor/localization sensor as set forth in claim 1, wherein the anchor is a surgical screw.

4. The integrated surgical anchor/localization sensor as set forth in claim 1, wherein the receiver includes at least one electromagnetic sensor.

5. The integrated surgical anchor/localization sensor as set forth in claim 3, wherein the screw contains an opening therein and where the connector includes potting material for securing at least the receiver within the opening.

6. The integrated surgical anchor/localization sensor as set forth in claim 1 wherein said integrated surgical anchor/localization sensor defines a working channel and wherein the plurality of collinear electromagnetic coils are wrapped around the working channel to minimize a size of the integrated surgical anchor/localization sensor.

7. An integrated surgical anchor/localization sensor, comprising:
    an anchor adapted to be secured to an anatomical structure;
    a receiver, for sensing signals generated by a surgical guidance system, wherein at least the receiver is selectively detachable from the anchor;
    a transmitter coupled to the receiver, for conveying to a processor signals received by the receiver; and
    a connector for securing at least the receiver to the anchor, the connector being configured so that the signals conveyed by the transmitter are indicative of a current position of the anchor.

8. The integrated surgical anchor/localization sensor as set forth in claim 7, wherein the transmitter includes at least one wire connected to the receiver for hardwiring the receiver to the processor.

9. The integrated surgical anchor/localization sensor as set forth in claim 7, wherein the transmitter is wireless.

10. The integrated surgical anchor/localization sensor as set forth in claim 7, wherein the receiver includes a conductive electrode.

11. The integrated surgical anchor/localization sensor as set forth in claim 7, wherein the connector includes a housing that mounts on the anchor.

12. The integrated surgical anchor/localization sensor as set forth in claim 7 wherein said connector is selectively detachable from the anchor.

13. An integrated surgical anchor/localization sensor, comprising:
    a threaded region;
    a grasping region for allowing at least a portion of the threaded region to be threaded into an anatomical structure;
    a sensor mounting portion, the sensor mounting portion being selectively detachable from the threaded region;
    a receiver at least partially contained within the sensor mounting portion, the receiver configured to sense reference signals generated by a surgical guidance system; and
    a transmitter coupled to the receiver, for transmitting, as a function of the sensed reference signals, positional signals indicative of a current position of the receiver.

14. The integrated surgical anchor/location sensor of claim 13, wherein the transmitter includes a wire for hardwiring the receiver to a surgical guidance system.

15. The integrated surgical anchor/location sensor of claim 13, wherein the transmitter is wireless.

16. The integrated surgical anchor/location sensor of claim 13, wherein the receiver includes at least one electromagnetic coil.

17. An integrated surgical anchor/localization sensor, comprising:
    a threaded region;
    a grasping region for allowing at least a portion of the threaded region to be threaded into an anatomical structure;
    a sensor mounting portion;
    a receiver at least partially contained within the sensor mounting portion, the receiver configured to sense reference signals generated by a surgical guidance system, the receiver includes a plurality of coils coaxially arranged and wound at differing angles; and
    a transmitter coupled to the receiver, for transmitting, as a function of the sensed reference signals, positional signals indicative of a current position of the receiver.

18. The integrated surgical anchor/location sensor of claim 17, wherein the receiver includes a conductive electrode configured to receive conductive localization signals.

19. A surgical localization sensor for integration into a tissue or bone anchor, the localization sensor comprising:
    a receiver for sensing reference signals generated by a surgical navigation system, the receiver including a plurality of electromagnetic coils coaxially arranged and wound at differing angles;
    a transmitter for conveying positional signals, as a function of a current location of the receiver and the reference signals generated by the surgical navigation system; and
    a connector for mounting at least the receiver to the anchor, the connector configured so that the positional signals conveyed by the transmitter reflect a current position of the anchor, wherein the connector includes a housing configured to be selectively detachable from the anchor.

20. The sensor of claim 19, wherein the receiver includes at least one electromagnetic coil.

21. The sensor of claim 19, wherein the receiver includes a conductive electrode.

22. The sensor of claim 19, wherein the transmitter includes a wire for hardwiring the sensor to a surgical localization system.

23. The sensor of claim 19, wherein the transmitter is wireless.

24. An integrated surgical anchor/localization sensor, comprising:
    an anchor adapted to be secured to an anatomical structure;

a signal generator for emitting signals to be processed by surgical navigation system circuitry; and a connector for securing the signal generator to the anchor, the connector being configured so that the signals emitted by the signal generator are indicative of a current position of the anchor and being configured to be selectively detachable from the anchor.

25. The integrated surgical anchor/localization sensor of claim 24, wherein the signal generator is an electromagnetic field generator.

26. The integrated surgical anchor/localization sensor of claim 24, wherein the signal generator is a magnet.

\* \* \* \* \*

UNITED STATES PATENT AND TRADEMARK OFFICE
CERTIFICATE OF CORRECTION

PATENT NO. : 6,499,488 B1
DATED : December 31, 2002
INVENTOR(S) : Michael A. Martinelli et al.

It is certified that error appears in the above-identified patent and that said Letters Patent is hereby corrected as shown below:

Title page,
Item [75], Inventors, insert -- Michael A. Martinelli, Winchester, MA -- before "Mark W. Hunter"

Signed and Sealed this

Twenty-eighth Day of June, 2005

JON W. DUDAS
*Director of the United States Patent and Trademark Office*